(12) United States Patent
Tomita et al.

(10) Patent No.: US 6,277,600 B1
(45) Date of Patent: Aug. 21, 2001

(54) TRIMERIC CHIMERA PROTEIN AND COLLAGEN MATRIX CONTAINING CHIMERA PROTEIN

(75) Inventors: Masahiro Tomita; Takashi Kitajima, both of Kanagawa (JP)

(73) Assignee: Terumo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/391,001

(22) Filed: Sep. 7, 1999

(30) Foreign Application Priority Data

Sep. 7, 1998 (JP) .................................................. 10-252178

(51) Int. Cl.[7] ............................. C12P 21/04; A61K 38/39
(52) U.S. Cl. ........................ 435/69.7; 435/69.1; 435/455; 530/300; 530/350; 530/356
(58) Field of Search .................................. 435/69.1, 69.7, 435/455, 252.3, 325, 320.1; 530/300, 350, 356

(56) References Cited

U.S. PATENT DOCUMENTS

| | | | |
|---|---|---|---|
| 5,405,757 | * 4/1995 | Prockop et al. | 435/69.1 |
| 5,686,059 | * 11/1997 | Goetinck et al. | 424/9.1 |
| 5,800,811 | * 9/1998 | Hall et al. | 424/93.7 |
| 5,856,308 | * 1/1999 | St. Pierre et al. | 514/18 |
| 5,925,736 | * 7/1999 | Neff et al. | 530/356 |

FOREIGN PATENT DOCUMENTS

| 8-23979 | 1/1996 | (JP) . |
|---|---|---|
| 8-253429 | 10/1996 | (JP) . |

OTHER PUBLICATIONS

Fujioka, K. et al., "Novel Delivery System for Proteins Using Collagen as a Carrier Material: the Minipellet", Journal of Control. Release, 33:307–315, 1995.

Lamberg, A. et al., "Characterization of Human Type III Collagen Expressed in a Baculovirus System", Jounal of Biol. Chem., 271:11988–11995, 1996.

Myllyharju, J. et al., "Expression of Wild–Type and Modified Prox Chains of Human Type I Procollagen in Insect Cells Leads to the Formation of Stable[x1(I)]$_2$x2(I) Collagen Heterotrimers and [x1(I)]$_3$ Homotrimers but Not [x2(I)]$_3$ Homotrimers", Journal of Biol. Chem. 272:21824–21830, 1997.

Tomita, M. et al., "Biosynthesis of Recombinant Human Pro–x1 (III) Chains in a Baculovirus Expression System: Production of Disulphide–Bonded and Non–Disulphide–B-onded Species Containing Full–Length Triple Helices", Biol. J. 312:847–853, 1995.

Tomita, M. et al., "Formation of Recombinant Human Procolagen I Heterotrimers in a Baculovirus Expression System", Journal of Biol. Chem., 121:1061–1069, 1997.

* cited by examiner

Primary Examiner—Kenneth R. Horlick
(74) Attorney, Agent, or Firm—Burns, Doane, Swecker & Mathis, LLP

(57) ABSTRACT

Provision of a trimeric chimera protein which has sufficiently retained physiological activity of a physiologically active peptide simultaneously with fibril-forming ability of a collagen. A trimeric chimera protein comprising a collagen and a biologically active peptide fused to the collagen, wherein the biologically active peptide is fused on the side of the amino terminal of the collagen, and the collagen is a fibril-forming collagen having a triple helical structure in its triple helix region.

27 Claims, 3 Drawing Sheets

SEQUENCE LISTING

```
<160> NUMBER OF SEQ ID NOS: 3

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:The
      oligonucleotide

<400> SEQUENCE: 1
cagaactatt ctctcccgta tgattcatat g                              31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:The primer

<400> SEQUENCE: 2
ctcaacacta actcgagaat taagtgcttc c                              31

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence:The primer

<400> SEQUENCE: 3
gacataatat gtgacgctcg agaattagac tgc                            33
```

TRIMERIC CHIMERA PROTEIN AND COLLAGEN MATRIX CONTAINING CHIMERA PROTEIN

TECHNICAL FIELD

This invention relates to a novel chimera protein comprising a collagen having covalently bonded thereto a biologically active peptide such as a cell growth factor or a cytokine; and a method for producing such chimera protein. This invention is also directed to a novel collagen matrix produced through fibril-formation of such chimera protein.

BACKGROUND ART

Collagen is a protein which is widely used in medical field as a biomaterial for restoring the body damage and as a carrier of various drugs. The collagens currently used for such applications are collagens of animal origin extracted from the tissue of cows, pigs, and the like. Use of a collagen of human origin is desirable in consideration of immunological reactions, and also, contamination of pathogens such as viruses and prions from animal tissues which is currently a serious issue. In view of such situation, the inventors of the present invention have proposed a method for producing a recombinant human collagen having a triple helical structure equivalent to the one found in human body by infecting insect cells with a recombinant virus having the cDNA coding for a human collagen inserted therein (JP-A 8-23979). This method is also described in Tomita et al., (Biochemical J. 312, 847–853 (1995) and J. Biochem. 121, 1061–1069 (1997)). And the similar methods are described in Lamberg et al., (J. Biol. Chem. 271, 11988–11995 (1996)), Myllyharju et al., (J. Biol. Chem. 272, 21824–21830 (1997)), Nokelainen et al., (Matrix Biology, 16, 329–338 (1998)).

Prockop et al. have also proposed a method for producing recombinant human collagens by using mammal cells or yeasts (JP-A 7-501939, Published Japanese Translation of WO93/07889). Ala-Kokko et al., (J. Biol. Chem. 266, 14175–14178 (1991)), Geddis et al., (Matrix 13, 399–405 (1993)) and Fertala et al., (Biochemical, J. 298, 31–37 (1994)) disclose the similar methods.

It is not clear whether a plurality of proteins having formed as fusion protein can always exhibit their own activities, because the activity of a protein is dependent on its conformation. Further, it is not clear whether a trimer of the fusion protein can be formed which retains the activities of the collagen and the peptide, because trimeric fusion protein containing essentially full length of collagen has not been heretofore reported.

On the other hand, cell growth factors, cytokines and various other biologically active peptides are highly hoped for use as a drug. These peptides, however, suffer from high elimination rate, and practical use of such biologically active peptides is often prevented by their high elimination rate. In order to obviate such situation, mixing of the biologically active peptide with the collagen and embedding of the mixture in the body for controlled release has been proposed (Fujioka et al., J. Controlled Release 33, 307 to 315, 1995). This reference describes that when interferon (INF) was mixed with gelatin or collagen and embedded in animal body the INF release from gelatin gel was 100% after 1 day, but the release from collagen gel was less than 100% though more than 60% after 1 day. It also describes that drying of the mixture of INF and collagen reduces the release rate of INF.

DISCLOSURE OF THE INVENTION

As described above, collagen is expected for its use as a carrier of various biologically active peptides which enable controlled release of the peptides. Affinity of the collagen for the biologically active peptide is not necessarily high, and the biologically active peptide is not stably retained in the collagen matrix for a prolonged period of time by merely mixing the biologically active peptides with the collagen. When the biologically active peptide is chemically bonded to the collagen using glutaraldehyde or the like, the biologically active peptide will undergo total or partial inactivation.

To solve the problem the present inventors have been studied whether the peptide of collagen and biologically active peptide could be produced as a single protein or not.

In view of the situation as described above, an object of the present invention is to provide a method for fusing a biologically active peptide to a collagen with no loss in the activity, and hence, to provide a novel trimeric chimera protein which is simultaneously provided with the features of the biologically active peptide and the collagen. Another object of the invention is to provide a novel collagen matrix produced by polymerizing the chimera protein.

In order to obviate the situation as described above, the inventors of the present invention have invented a method for producing a recombinant chimera protein wherein the chimera protein is produced by ligating the gene coding for a procollagen and the gene coding for a biologically active peptide by genetic engineering means, and the ligation product is expressed by using a recombinant protein expression system. As described above, various methods are reported to produce collagen with native conformation by recombinant method. In these reports there are not any indications of the technical possibilities to produce a chimera protein of biologically active peptide and collagen. There have been no attempt to produce such a chimera protein in the prior art.

Furthermore, the inventors invented a collagen matrix comprising collagen fiber which is produced through polymerizing such chimera protein either alone or after mixing with collagen molecule. The present invention was thereby completed. In other words, the objects of the present invention are attained by means of (1) to (14) as described below.

(1) A trimeric chimera protein comprising a collagen and a biologically active peptide fused to the collagen, wherein said biologically active peptide is fused on the side of the amino terminal of the collagen, and the collagen is a fibril-forming collagen having a triple helical structure in its triple helix region.

In this invention, biologically active peptide means a peptide having a biological activity to vary all kinds of cellular function, such as proliferation, migration, gene expression, differentiation and the like.

(2) A trimeric chimera protein according to the above (1) wherein said trimeric chimera protein substantially lacks carboxyl propeptide region of the procollagen which is a collagen precursor; or said carboxyl propeptide region has been substituted with a peptide which does not inhibit fibril-formation and which is capable of forming the urimer.

(3) A trimeric chimera protein according to the above (1) or (2) wherein said biologically active peptide is directly fused to the amino terminal of the triple helix region of the collagen; or a part of the amino propeptide region of the collagen precursor procollagen is inserted at the fusion site of the biologically active peptide and the collagen.

(4) A trimeric chimera protein according to the above (1) or (2) wherein full or substantially full length of the amino propeptide region of the procollagen is inserted in the fusion site of the biologically active peptide and the collagen.

(5) A collagen matrix comprising collagen fiber containing a chimera protein comprising a collagen and a biologically active peptide fused to the amino terminal of the collagen as its constituent.

(6) A collagen matrix according to the above (5) wherein said collagen fiber comprises a mixture of a chimera protein and a collagen molecule.

(7) A collagen matrix according to the above (6) wherein said chimera protein is uniformly distributed in the collagen fiber, and the portion of said biologically active peptide is embedded in the collagen fiber.

(8) A collagen matrix according to the above (7) wherein said chimera protein is a trimeric chimera protein of any one of the above (1) to (3).

(9) A collagen matrix according to the above (6) wherein said chimera protein is distributed in the surface region of said collagen fiber, and said biologically active peptide protrudes beyond the surface of said collagen fiber.

(10) A collagen matrix according to the above (9) wherein said chimera protein is a trimeric chimera protein of any one of the above (1), (2) or (4).

(11) A method for producing a trimeric chimera protein wherein a trimeric chimera protein of any one of the above (1) to (4) is produced by ligating the gene coding for a procollagen and the gene coding for a biologically active peptide by genetic engineering means, and expressing the ligation product using a recombinant protein expression system.

(12) A method for producing a trimeric chimera protein according to the above (11) wherein said recombinant protein expression system is a baculovirus expression system.

(13) A vector for expressing a trimeric chimera protein of any one of the above (1) to (4), said vector containing the gene coding for a procollagen and the gene coding for a biologically active peptide.

(14) Cells for producing a trimeric chimera protein of any one of the above (1) to (4), said cells having the vector of the above (13) incorporated therein.

BRIEF DESCRIPTION OF DRAWINGS

FIG. 2 A, B and C are an each electrophoretic diagram showing the immunoreactivity of the chimera protein.

BEST MODE FOR CARRYING OUT THE INVENTION

The present invention is described in further detail. Of the 19 different types of collagens so far found, types I, II, III, V and XI are referred to as fibril-forming collagens since collagens of these types polymerize to form a water-insoluble fibrillar structure (collagen fibrils or fibers, Kielty et al., Connective Tissue and Its Heritable Disorders, Chapter 3, Wiley and Lis, Inc. (1993)). These fibril-forming collagens are provided with uninterrupted triple helical structure of about 300 nm in length, and molecules of these fibril-rorming collagens undergo spontaneous polymerization under physiological conditions. The resulting collagen fibrils or fibers intertwine with each other to form a collagen matrix.

In the biosynthesis of the fibril-forming collagen, a precursor, namely, procollagen is first synthesized. The procollagen is synthesized as the precursor in all types of fibril-forming collagens, and the procollagen molecules have the common structure comprising a triple helix region provided with an amino propeptide region on its amino terminal and a carboxyl propeptide region on its carboxyl terminal. In the course of the formation of the triple helical structure of the procollagen, three pro α-chains constituting a helical molecule first associate at the carboxyl propeptide regions, and the three chains zip together in the direction of from the carboxyl terminal to the amino terminal. Therefore, in the present invention, the biologically active peptide is fused to the procollagen on the side of the amino terminal so that the fusion of them does not prevent the triple helix formation. The fusion site of the biologically active peptide on the amino terminal side of the procollagen may be either the amino terminal of the amino propeptide, or the amino terminal formed after removal of a part or all of the amino propeptide. As long as no adverse effects on the triple helix formation are induced, the fusion site may have other amino acid sequence inserted therein. The carboxyl propeptide region which plays an important role in the formation of the triple helical structure is removed after the formation of the triple helical structure of the chimera protein.

The production of the chimera protein is accomplished by ligating the cDNA coding for the biologically active peptide and the cDNA coding for the procollagen with no frame shift, and expressing the ligated cDNA from a recombinant protein expression system. The ligation of the cDNAs may be accomplished, for example, by introducing the same restriction enzyme site in the region immediately before the termination codon of the cDNA for the biologically active peptide and in the nucleotide sequence coding for the amino propeptide region of the procollagen cDNA. The procollagen cDNA used may be any of the cDNAs coding for the fibril-forming collagens of type I, II, III, V, and XI. These concrete cDNA sequences are described respectively in known references in the prior art or references cited in this specification. As long as not to adversely effect on this invention, the cDNA described in the references may be substituted, deleted, inserted or added by another cDNA or cDNAs. Hybridizable DNA with the cDNA may also be used.

The term "biologically active peptides" used herein generally designates proteins and peptides which have various biological activities. Typical biologically active peptides include growth factors such as fibroblast growth factors (FGFs), transforming growth factors (TGFs), bone morphogenetic proteins (BMPs), epidermal growth factors (EGFs), platelet derived growth factor (PDGF), insulin-like growth factors (IGFs), insulin, nerve growth factor (NGF), vascular endothelial growth factor (VEGF), and hepatocyLe growth factor (HGF); cytokines such as interferons (INFs), interleukins (ILs), colony stimulating factors (CSFs), erythropoietin, and tumor necrosis factors (TNFs); and various hormones and enzymes. These concrete cDNA sequences coding for the biologically active peptides are described in known references in the prior art or references cited in this specification respectively. As long as not to adversely effect on this invention, the cDNA described in the references may be substituted, deleted, inserted or added by another cDNA or cDNAs. Hybridizable DNA with the cDNA may also be used.

In order to enable fibril-formation of the chimera protein including the biologically active peptide and the procollagen to thereby produce the insoluble collagen matrix, the chimera protein should have the triple helical structure inherent to the collagen. Therefore, the recombinant protein expression system used in the present invention should be capable of synthesizing a procollagen which has the triple helical structure. In other words, the host of the expression system should have activities of collagen modification enzymes including prolyl hydroxylase activity required for the formation of the triple helical structure. The expression system used may be any system as long as the system is provided with such ability. An exemplary system is a baculovirus expression system of the present inventors (JP-A 8-23979) wherein insect cells with prolyl hydroxylase activity are utilized as the host.

In the normal biosynthesis of collagen, removal of the amino propeptide of the procollagen takes place after the secretion of the procollagen through recognition by N-proteinase of a particular sequence at the boundary between the amino propeptide region and the triple helix region and cleavage at the recognized site (Kielty et al., Connective Tissue and Its Heritable Disorders, Chapter 3, Wiley and Lis, Inc. (1993)). In the present invention, the amino acid sequence recognized by the proteinase may be altered when stable connection of the biologically active peptide and the procollagen is desired. Such alteration may be accomplished by substituting the nucleotide sequence coding for the amino propeptide cleavage sequence with an appropriate sequence by means of, for example, site-directed mutagenesis. For example, the nucleotide sequence coding for the amino acid sequence Pro-Gln in the N-proteinase cleavage site of type III procollagen is changed to the nucleotide sequence coding for Leu-Pro.

However, such alteration of the cleavage site is not required when release of the biologically active peptide from the chimera protein by cleavage with N-proteinase is desired.

Carboxyl propeptide plays an important role in the formation of the triple helical structure of the procollagen. Carboxyl propeptide, however, prevents further fibril-formation of the triple helical molecules. Accordingly, fibril-formation of the chimera protein is enabled, for example, by removing the carboxyl propeptide from the chimera protein including the biologically active peptide and the procollagen after the triple helix formation. Such removal of the carboxyl propeptide may be accomplished by using C-proteinase/BMP-1 (Kessler et al., Science 271, 360–362 (1996)), a proteinase that cleaves the boundary between the triple helix region and the carboxyl propeptide region. Alternatively, an amino acid sequence which is recognized and cleaved by a protease such as factor Xa or enterokinase may be inserted in the boundary between the triple helix region and the carboxyl propeptide region, and the carboxyl propeptide may be removed by such enzyme.

Fibril-formation of the chimera protein may be also enabled by substituting the carboxyl propeptide of the chimera protein with a peptide from a trimer forming protein such as transmembrane domain of influenza virus hemagglutinin. It should be noted that formation of a trimer procollagen molecule having the triple helical structure is already confirmed for the molecule wherein the carboxyl propeptide of the procollagen is substituted with the transmembrane domain of the influenza virus hemagglutinin (Bulleid et al., EMBO J. 16, 6694–6701, (1997)). This peptide, which comprises a short sequence of about 30 amino acid residues, will not hinder the fibril-formation of the chimera protein according to the present invention. The substitution of the carboxyl propeptide region may be accomplished by substituting the nucleotide sequence coding for the carboxyl propeptide of the procollagen cDNA with the nucleotide sequence coding for the transmembrane domain of the influenza virus hemagglutinin and expressing in a recombinant protein expression system as in the case of substituting the amino propeptide region with the biologically active peptide.

The chimera protein of the invention can form a trimer and retains the activity of the biologically active peptide, and hence has an industrially high utility. The collagen must be a trimer in order to form the insoluble collagen matrix by spontaneous polymerization. The biologically active peptide cannot be immobilized on the surface or inside of the collagen matrix without obtaining a trimeric chimera protein retaining the biological activity.

A collagen matrix having the activity of the biologically active peptide may be produced by incubating the trimeric chimera protein which is substantially free from the carboxyl propeptide or the chimera protein having its carboxyl propeptide substituted with a peptide from a trimer forming protein such as transmembrane domain of influenza virus hemagglutinin either alone or after mixing with native collagen of animal tissue origin under physiological conditions to thereby facilitate fibril-formation. The chimera protein may be mixed with the native collagen at a mole ratio of at least $10^{-12}$ chimera protein to 1 native collagen to realize the activity of the physiologically active peptide; up to $10^{-1}$ chimera protein to 1 native collagen to avoid hindrance of collagen fibril-formation by the chimera protein. The mole ratio, however, may vary depending on the type of the physiologically active peptide.

During polymerization of the chimera protein after mixing with native collagen, the chimera protein is incorporated into the collagen fiber in one of the two modes (1) and (2) as described below depending on the presence/absence of the amino propeptide at the fusion site of the physiologically active peptide and the collagen.

(1) In the substantial absence of the amino propeptide

Figure 1A:
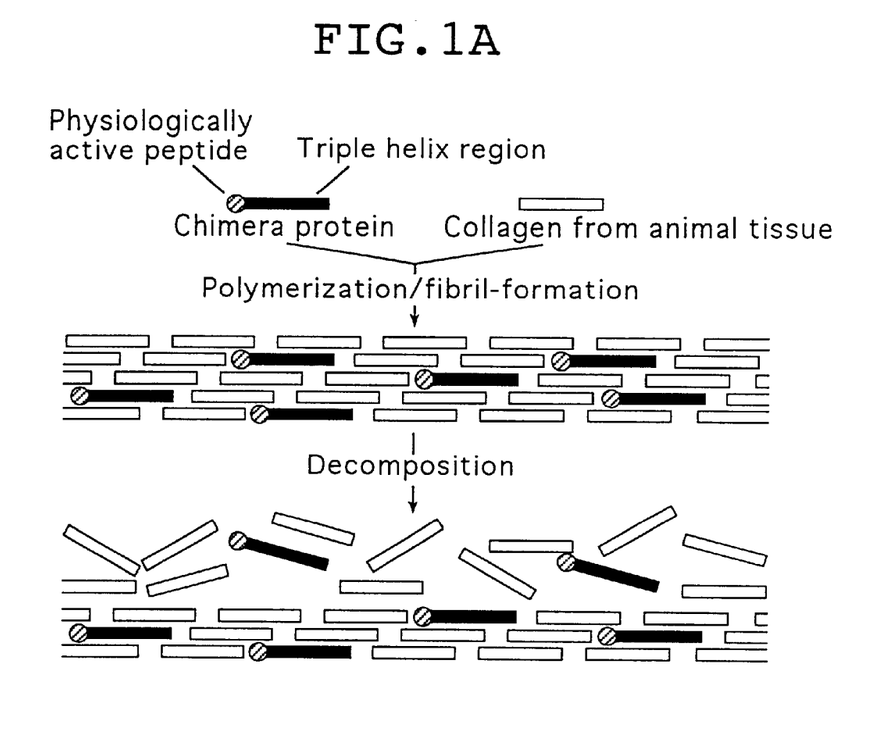
FIGS. 1A and 1B are schematic views respectively showing the production process and the structure of collagen matrix by using the chimera protein of the present invention.

When a chimera protein wherein all or most of the amino propeptide region is substituted with a biologically active peptide, namely, a chimera protein substantially lacking the amino propeptide region is used, the collagen matrix is preferably formed through fibril-formation such that the chimera protein is uniformly distributed in the collagen fibers and the biologically active peptide is embedded in the collagen fibers (FIG. 1A). When such collagen matrix is grafted in the living body, the biologically active peptide embedded in the collagen fiber which is stably maintained without being attacked by the protease will be slowly released from the collagen matrix with decomposition of the collagen in the body. The residential period of the collagen matrix in the body ranges from several weeks to several months depending on the production process of collagen matrix, and the biologically active peptide will be slowly released from the collagen matrix until the matrix is fully decomposed. Such collagen matrix may be produced by mixing the chimera protein and the native collagen in a solution of physiological salt concentration and pH, and promoting the fibril-formation by incubation at the physiological temperature. The domain of the biologically active peptide in the chimera protein incorporated in the collagen fiber is embedded in the gaps formed between the collagen molecules formed during the fibril-formation.

(2) In the substantial presence of the amino propeptide

Figure 1B:
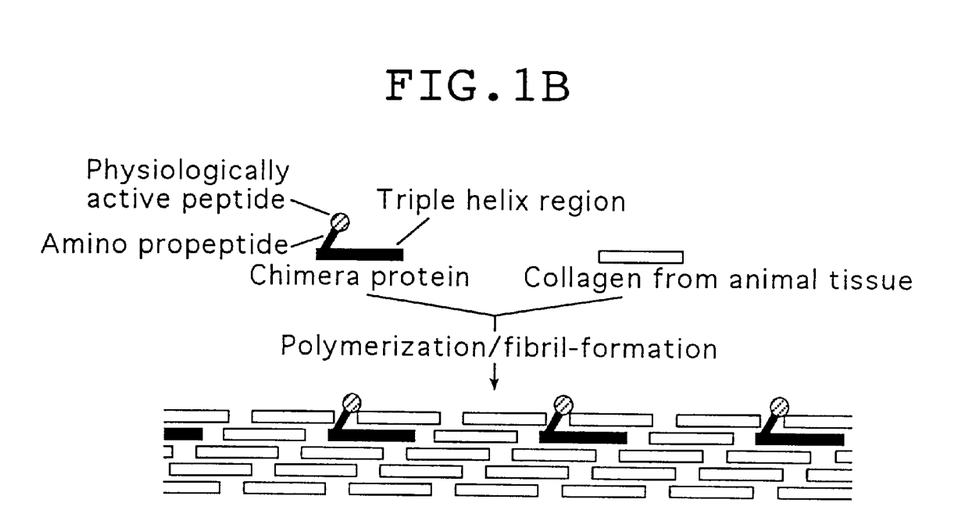

When a chimera protein wherein the biologically active peptide is fused at the amino terminal or near the amino terminal of the amino propeptide region with most of the amino propeptide left, namely, a chimera protein substantially including the amino propeptide region is used, the collagen matrix is preferably formed through fibril-formation such that the chimera protein is incorporated in the collagen fibers with the biologically active peptide protruding beyond the fibers via the intervening amino propeptide (FIG. 1B). When such collagen matrix is grafted in the living body, an extremely local drug delivery is realized wherein the biologically active peptide acts only upon contact of the particular cells with the collagen matrix. The collagen matrix may be produced as in the case of above (1) by mixing the chimera protein and the native collagen in a solution of physiological salt concentration and pH, and promoting the fibril-formation by incubation at the physiological temperature. In the course of fibril-formation, the amino propeptide region of the chimera protein will be bent at a particular angle in relation to the triple helix region so as not to avoid the fibril-formation, and thus the biologically active peptide will spontaneously protrude beyond the surface of the fibers.

EXAMPLES

Next, the present invention is described in further detail by referring to an example wherein a chimera protein of interleukin-2 (IL-2) and type III collagen is produced by using a baculovirus expression system. The present invention is not limited to such examples.

A. Preparation of an expression vector for a chimera protein wherein IL-2 is fused to type III collagen including amino propeptide The cDNA coding for the human type III procollagen used was the one cloned by the inventors and was described in the previous invention (JP-A 8-23979). The nucleotide sequence of this cDNA is the same one reported by Ala-Kokko et al., (Biochem. J., 260, 508–517 (1989)). The cDNA coding for the human IL-2 was the one having a sequence the same as the one inserted in pIL2-50A (Taniguchi et al., Nature 302, 305–310, (1983)). The nucleotide numbers of the cDNAs of the human type III procollagen and the human IL-2 are based on the nucleotide numbers of Accession Nos. X14420 and U25676 registered in GeneBank database.

(1) Alteration of the Procollagen Amino Propeptide Cleaving Sequence

Oligonucleotide 5' CAGAACTATTCTCTCC CGTATGATTCATATG 3' was synthesized. This sequence corresponds to the nucleotide sequence of nucleotide numbers 547 to 577 of human type III procollagen, and the underlined nucleotides T and C have been altered from C and A in the original procollagen nucleotide sequence. By using this oligonucleotide for the primer, C at nucleotide number 560 was altered to T, and A at nucleotide number 563 was altered to C in the cDNA of type III procollagen by site-directed mutagenesis (Deng and Nickoloff, Anal. Biochem., 200, 81–88(1992)) using in vitro mutagenesis kit (Clontech). By these alteration, the nucleotide sequence coding for the amino acid sequence Pro-Gln in the N-proteinase cleavage site was changed to the nucleotide sequence coding for Leu-Pro.

(2) Ligation of IL-2 cDNA and Type III Procollagen cDNA, and Preparation of a Baculovirus Transfer Vector The XhoI restriction site was introduced immediately before the termination codon of IL-2cDNA (nucleotide numbers 514 to 519) and within the nucleotide sequence coding for the amino propeptide of the type III procollagen cDNA (nucleotide numbers 308–313) by the site-directed mutanegensis as described above. The primers employed had the nucleotide sequences 5' CTCAACACTA ACTCGAGAATTAAGTGCTTCC 3' (SEQ ID NO: 2)and 5' GACATAATATGTGACGCTCGAGAATTAGACTGC 3', and these sequences corresponded to nucleotide numbers 503 to 533 of the IL-2 cDNA and nucleotide numbers 292 to 324 of the type III procollagen cDNA. As shown by the underlines, the primers had XhoI restriction site inserted therein. Next, the cDNAs respectively having the XhoI restriction site introduced therein were cleaved by XhoI, and then ligated with T4 DNA ligase. The resulting cDNA was inserted at the BamHI restriction site of a baculovirus transfer vector pAcYM1 (Matsuura et al., J. Gen. Virol., 173, 674–682 (1987)) to obtain a transfer vector pAcIL2-3A1. A transfer vector for control experiment was also prepared by inserting only IL-2 cDNA in the BamHI restriction site of pAcYM1.

(3) Preparation of Recombinant Virus

To 8 µl of sterilized water were dissolved 2 µg of the DNA of the plasmid pAcIL2-3A1 obtained in the above (2) and 100 ng of linearized baculovirus DNA (BaculoGold, Pharmingen). The solution was mixed with 8 µl of two fold diluted lipofec-in (Gibco), and allowed to stand at room temperature for 15 minutes. The mixture was then added for transfection to 1×10⁶ Sf9 cells which had been cultured in Grace's medium (Gibco) containing 10% fetal bovine serum and the medium had been exchanged with a serum free medium SF900-II (Gibco). The transfected cells were cultured at 28° C. for 4 days, and the culture supernatant was recovered. A part of the culture supernatant was used to infect Sf9 cells which had been cultivated separately, and the infected cells were overlaid with the above-described medium containing 1% agarose and solidified. After incubating for 3 days, the plaque developed was removed together with the agarose to obtain recombinant virus AcIL2-3A1 wherein homologous recombination had taken place between pAcIL2-3A1 and the baculovirus genome DNA. 1×10⁶ Sf9 cells were infected with the recombinant virus, and the cells were cultured at 28° C. for 3 days. The recombinant virus released into the culture medium was collected. The infection process was repeated again, and recombinant virus AcIL2-3A1 was finally obtained at 1×10⁸ p.f.u./ml. A recombinant virus AcIL2 was also produced from transfer vector pAcIL2 as described above.

B. Expression of the Chimera Protein of IL-2 and Type III Procollagen

1×10⁶ Sf9 cells were infected with thus obtained AcIL2-3A1 virus to a multiplicity of infection of 10. The infected cells were cultured in Grace's medium supplemented with 10% fetal bovine serum at 28° C. for 48 hours, and the culture medium was collected and ammonium sulfate was added to the medium to 30% saturation. After allowing to stand at 4° C. for 16 hours, the medium was centrifuged at 10,000 g at 40° C. for 30 minutes. The protein precipitate was dissolved in 20 mM Tris-HCl, pH 7.5/150 mM NaCl. Sf9 cells were also infected with AcIL2 and Ac3Al (human type III procollagen recombinant virus described in JP-A 8-23979) by the procedure as described above to recover the protein in the culture medium.

Figure 2:
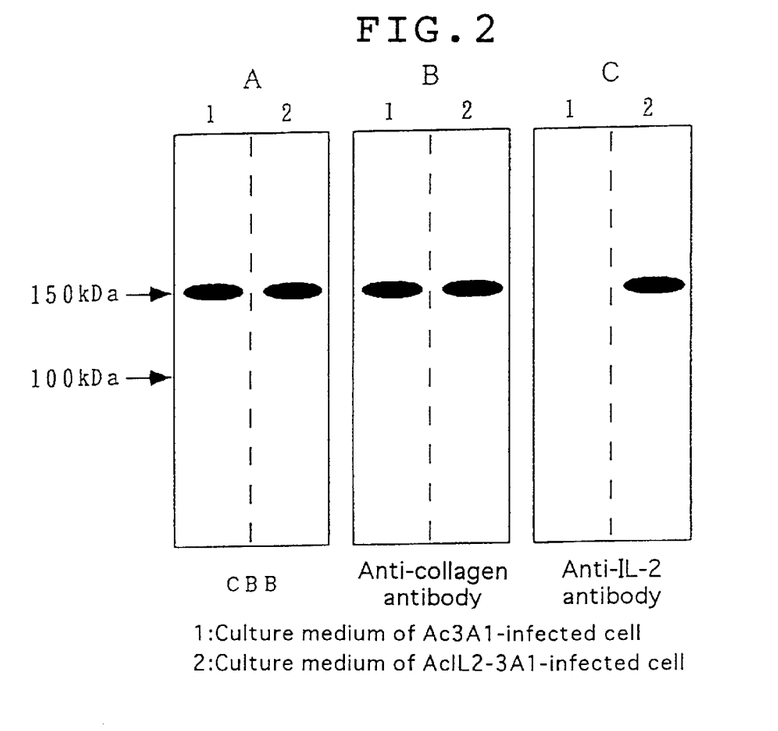

C. Confirmation of the Recombinant Product 20 µl of protein samples recovered from the culture medium of the cells infected with Ac3AI virus or AcIL2-3A1 virus were respectively mixed with 20 pl of 2XSDS-sample buffer (0.25 M Tris-HCl buffer solution, pH 6.8/4% SDS/10% 2-mercaptoethanol/20% glycerol), and the mixtures were boiled at 100° C. for 5 minutes. 15 µl of the boiled sample was subjected to SDS-PAGE (Laemmli, Nature 227, 680–685 (1970)), and the gel was stained by protein staining with Coomasie-Brilliant Blue. As a consequence, bands which were estimated to be recombinant proteins from Ac3A1 and AcIL2-3A1 were found at the position of 150 kDa as shown in FIG. 2, A.

In addition, after the electrophoresis of the samples as described above, the electrophoresed proteins were also transferred to nitrocellulose membrane BA85 (S&S) according to the method of Matsudaira (J. Biol. Chem. 261, 10035–10038 (1987)). The nitrocellulose membrane having the protein -transferred thereto was treated with a blocking solution (3% BAS/50 mM Tris-HCl, pH 7.5/150 mM NaCl) at 4° C. for 16 hours, and reacted at room temperature for 1 hour with anti-human/bovine type III collagen antibody (LSL) or anti-human IL-2 antibody (Chemicon) which had been diluted 1:200 in the blocking solution. The proteins reacted with these antibodies were detected with Vectastain ABC kit (Vector Laboratory), and it was then confirmed that the protein of 150 kDa from the Ac3A1 infected cells only reacts with the type III collagen antibody, and the protein from AcIL2-3A1 infected cells reacts with both the type III collagen antibody and the IL-2 antibody (FIGS. 2, B and C). It was then concluded that the protein of about 150 kDa synthesized by the Sf9 cells infected with the recombinant virus AcIL2-3A1 was the IL-2-type III procollagen chimera protein.

Figure 3:
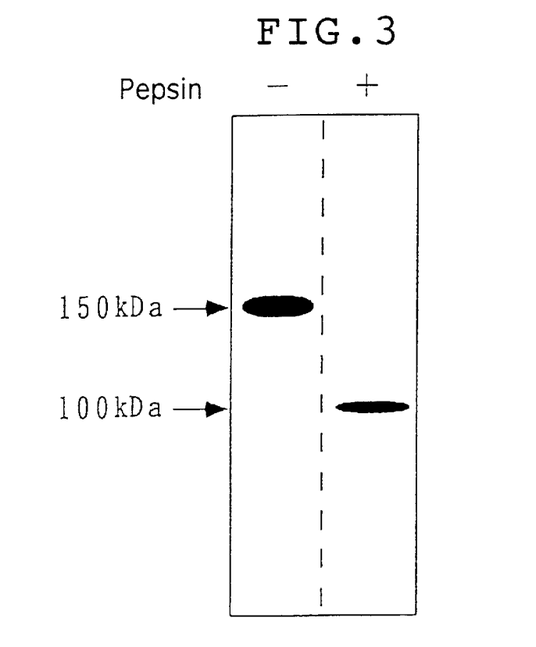
FIG. 3 is an electrophoretic diagram indicating the triple helical structure of the chimera protein.

D. Confirmation of Triple Helical Structure in IL-2-type III Procollagen Chimera Protein Triple helical structure of the collagen is not digested with a protease such as pepsin or trypsin. As a consequence, when a digestion product of the procollagen having such triple helical structure is subjected to electrophoresis after treating with a protease, band of only the triple helix region having a molecular weight of about 100 kDa is detected. Presence of the triple helical structure in the IL-2-type III procollagen chimera protein was confirmed by utilizing this principle. More illustratively, after lyophilizing the protein samples in the above "B", pepsin dissolved in 0.5M acetic acid at a concentration of 100 µg/ml was added to the lyophilized sample and the treatment was conducted at 4° C. for 16 hours. After the treatment, the solution was neutralized with iN NaOH, and 2×SDS-sample buffer was added. The protein samples were electrophoresed by the procedure as described in the above "C", and stained by protein staining with Coomasie-Brilliant Blue. As a consequence, the band of the IL-2-type III procollagen chimera protein with the size of about 150 kDa that had been present before the pepsin treatment disappeared, and a new band of 100 kDa newly appeared as shown in FIG. 3. This change in the molecular weight indicates removal by decomposition of the IL-2 domain and the propeptide region from the chimera protein and conversion into the triple helical collagen molecule. The results as described above indicate that the IL-2-type III procollagen chimera protein synthesized by the Sf9 cells is a trimer molecule that has a triple helical structure.

E. Measurement of the Activity of the IL-2-type III Procollagen Chimera Protein

Figure 4:
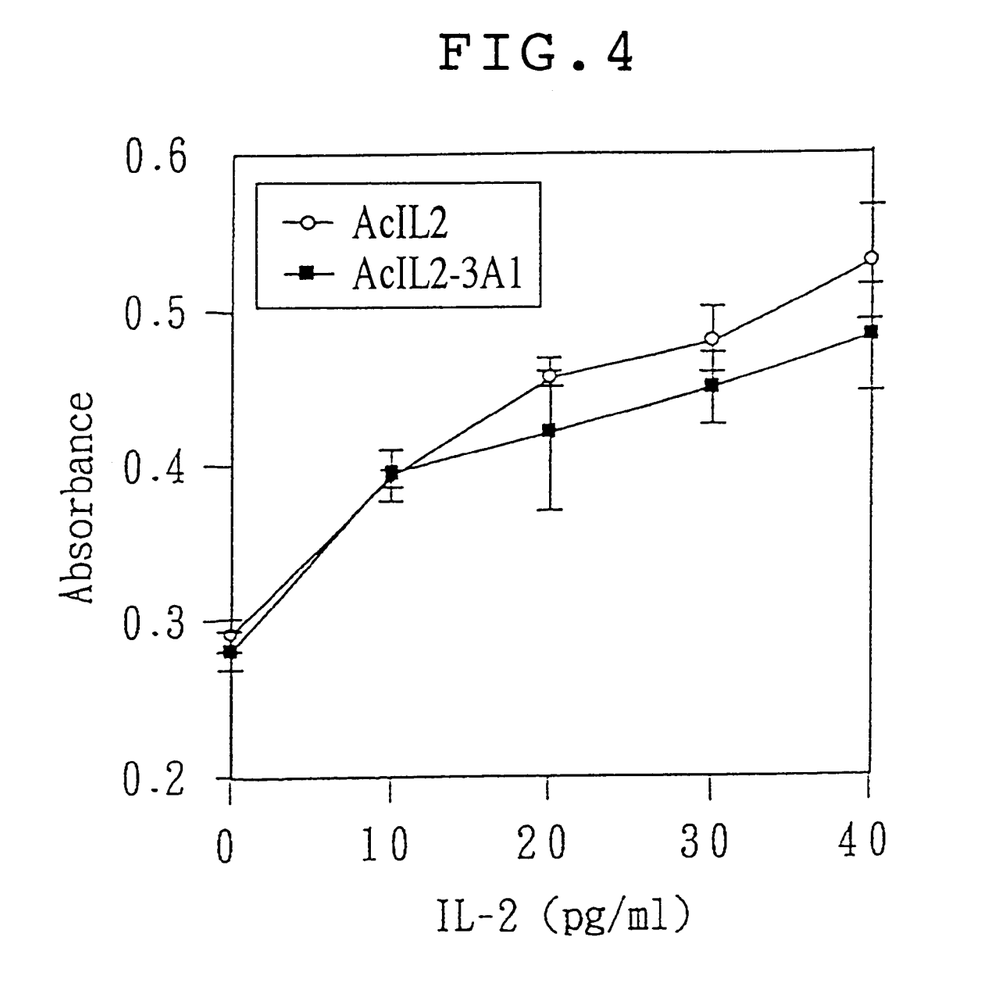
FIG. 4 is a graph showing biological activity of the chimera protein.

Proliferation of mouse CTLL2 cell (Gillis and Smith, Nature 268, 154–156 (1977)) which is an IL-2 dependent cell line was measured by MTT method to determine whether the activity of the IL-2 fused to the type III procollagen is retained. A suspension (10 µl) of CTLL2 cells in RPMI1640 medium (Gibco) supplemented with 10% fetal bovine serum was dispensed in wells of 96 well plate at $10^4$ cells/well, and the culture medium of AcIL2-3A1 or AcIL2 infected cells was added to the suspension. The culture medium of the infected cells had been determined for its IL-2 concentration by using ELISA kit (Endogen). The CTLL2 cells supplemented with the culture medium was cultivated for 24 hours, supplemented with MTT reagent (Chemicon), and further cultivated. After 4 hours, MTT formazan precipitate formed in the wells was dissolved by adding 0.04N HCl/isopropanol, and absorbance was measured at a wavelength of 630 nm. As a consequence, an activity of the IL-2-type III procollagen chimera protein substantially equivalent to that of IL-2 was confirmed as shown in FIG. 4.

F. Production of a Collagen Matrix Having the Chimera Protein Incorporated Therein The trimer of IL-2-type III procollagen chimera protein from which carboxyl propeptide had been removed was mixed with bovine skin type I collagen solution. The mixture was incubated in a buffer (pH 7.4) containing 150 mM NaCl at 37° C. for more than 30 minutes to polymerize the collagen. The IL-2-type III collagen chimera protein was thus immobilized in the collagen matrix.

As described above, the present invention provides a trimeric chimera protein wherein physiological activity of the physiologically active peptide and fibril-forming activity of the collagen are maintained. In other words, the present invention has enabled to produce various chimera proteins which are simultaneously provided with the functions of the physiologically active peptides and the collagen. Also provided is a collagen matrix which can be used in preparing novel controlled release drugs and the like wherein the physiologically active peptide stably incorporated in the collagen matrix is released as the collagen is decomposed in the body. Since functional modification of collagen with new physiological activity has been enabled by the present invention, new collagen matrices for medical use can be developed and used as new biomaterials adapted for remedy of damaged tissues.

REFERENCE

All the foregoing and following published works and pending patent applications cited herein are hereby expressly incorporated by reference in full.

Tomita, M. et al., "Biosynthesis of recombinant human pro-α1(III) chains in a baculovirus expression system: production of disulphide-bonded and non-disulphide-bonded species containing full-length triple helices" Biochem. J., 312:847–853, 1995.

Tomita, M. et al., "Formation of recombinant human procollagen I heterotrimers in a baculovirus expression system" J. Biochem., 121:1061–1069, 1997

Lamberg, A. et al., "Characterization of human type III collagen expressed in a baculovirus system" J. Biol. Chem., 271:11988–11995, 1996

Myllyharju, J. et al., "Expression of wild-type and modified prou chains of human type I procollagen in insect cells leads to the formation of stable $[(\alpha1(I)]_2(2(I)$ collagen heterotrimers and $[\alpha1(I)]_3$ homotrimers but not $[\alpha2(I)]_3$ homotrimers", J. Biol. Chem. 272:21824–21830, 1997.

Nokelainen, M. et al., "Expression and characterization of recombinant human type II collagens with low and high contents of hydroxylysine and its glycosylabed fiorms" Matrix Biol. 16:329–338, 1998

Ala-Kokko, L. "Expre ssion of a human cartilage procollagen gene (COL2A!) in mouse 3T3 cells", J. Biol. Chem., 266:14175–14178, 1991.

Geddis, A. E. and Prockop, D. J., "Expression of human COL1A1 gene in stably transfected HT1080 cells: The production of a thermostable homotrimer of type I collagen in a recombinant system", Matrix, 13:399–406, 1993 ertala, A. et al., "Synthesis of recombinant human procollagen II in a stably transfected tumour cell line (HT1080)", Biochem. J., 298:31–37, 1994.

Fujioka, K. et al., "Novel delivery system for proteins using collagen as a carrier material: the minipellet", J. Control. Pelease, 33:307–315, 1995.

Kielty, C. M. et al., "Collagen: The collagen family: Structure, assembly, and organization in the extracellular matrix" in Connective Tissue and Its Heritable Disorders, pp. 103–147. Wiley and Liss, Inc., 1993

Kessler, E. et al., "Bone morphogenetic protein-1: The type I procollagen C-proteinase", Science, 271:360–362, 1996.

Bulleid, N. J. et al., "The C-propeptide domain of procollagen can be replaced with a transmembrane domain without affecting trimer formation or collagen triple helix folding during biosynthesis", EMBO J., 16:6694–6701, 1997.

Ala-Kokko, L. et al., "Structure of cDNA clones coding for the entire preproul(III) chain of human type III procollagen. Differences in protein structure from type I procollagen and conservation of codon preferences", Biochem. J., 260:508–517, 1989.

Taniguchi, T. et al., "Structure and expression of a cloned cDNA for human interleukin-2", Nature 302:305–310, 1983.

Deng, W. J. and Nickoloff, J. A., "Site-directed mutagenesis of virtually any plasmid by eliminating a unique site", Anal. Biochem., 200:81–88, 1992.

Matsuura, Y. et al., "Characterization of Japanese encephalitis virus envelope protein expressed by recombinant baculovirus", Virology, 173:674–682, 1989.

Laemmli, U. K., "Cleavage of structural proteins during the assembly of the head of bacteriophage T4", Nature 227:680–685, 1970.

Matsudaira, P., "Sequence from picomole quantities of proteins electroblotted onto polyvinylidene difluoride membranes", J. Biol. Chem., 262:10035–10038.

What is claimed is:

1. A trimeric chimera protein comprising a collagen and a biologically active peptide fused to the collagen, wherein said biologically active peptide is fused on the side of the amino terminal of the collagen, and the collagen is a fibril-forming collagen having a triple helical structure region.

2. A trimeric chimera protein according to claim 1 wherein said trimeric chimera protein lacks a carboxyl peptide essential region of a procollagen precursor or said carboxyl propeptide region has been substituted with a peptide which does not inhibit fibril-formation and which is capable of forming the trimer.

3. A trimeric chimera protein according to claim 1 wherein said biologically active peptide is directly fused to the amino terminal of the triple helix region of the collagen or said biologically active peptide is fused to the amino terminal of the triple helix region of the collage via a peptide linker wherein said linker is a portion of the amino propeptide essential region of the collagen.

4. A trimeric chimera protein according to claim 1 wherein an amino propeptide essential region of the procollagen is inserted in the fusion site of the biologically active peptide and the collagen.

5. A collagen matrix comprising collagen fiber containing a chimera protein comprising a collagen and a biologically active peptide fused to the amino terminal of the collagen as its constituent.

6. A collagen matrix according to claim 5 wherein said collagen fiber comprises a mixture of a chimera protein and a collagen molecule.

7. A collagen matrix according to claim 6 wherein said chimera protein is uniformly distributed in the collagen fiber, and the portion of said biologically active peptide is embedded in the collagen fiber.

8. A collagen matrix according to claims 7 wherein said chimera protein is a trimeric protein comprising a collagen and a biologically active peptide fused to the collagen, wherein said biologically active peptide is fused on the side of the amino terminal of the collagen, and the collagen is a fibril-forming collagen having a triple helical structure region.

9. A collagen matrix according to claim 6 wherein said chimera protein is distributed in the surface region of said collagen fiber, and said biologically active peptide protrudes beyond the surface of said collagen fiber.

10. A collagen matrix according to claim 9 wherein said chimera protein is a trimeric chimera protein comprising a collagen and a biologically active peptide fused to the collagen, wherein said biologically active peptide is fused on the side of the amino terminal of the collagen, and the collagen is a fibril-forming collagen having a triple helical structure region.

11. A method for producing a trimeric chimera protein wherein a trimeric chimera protein of claim 1 is produced by ligating a gene coding for a procollagen and a gene coding for a biologically active peptide by genetic engineering means, and expressing the ligation product using a recombinant protein expression system.

12. A method for producing a trimeric chimera protein according to claim 11 wherein said recombinant protein expression system is a baculovirus expression system.

13. A vector for expressing a trimeric chimera protein of claim 1, said vector containing a gene coding for a procollagen and a gene coding for a biologically active peptide.

14. A cell for producing a trimeric chimera protein of claim 1, said cell having a vector containing a gene coding for a procollagen and a gene coding for a biologically active peptide.

15. A trimeric chimera protein according to claim 2, wherein said biologically active peptide is directly fused to the amino terminal of the triple helix region of the collagen or said biologically active peptide is fused to the amino terminal of the triple helix region of the collagen via a peptide linker, wherein said linker is a portion of the amino propeptide region of the collagen.

16. A trimeric chimera protein according to claim 2 wherein an amino propeptide essential region of the procollagen is inserted in the fusion site of the biologically active peptide and the collagen.

17. A collagen matrix according to claim 7, wherein said chimera protein lacks a carboxyl propeptide essential region of a procollagen or said carboxyl propeptide region has been substituted with a peptide which does not inhibit fibril-formation and which is capable of forming a trimer.

18. A collagen matrix according to claim 9, wherein said trimeric chimera protein lacks a carboxyl propeptide essential region of a procollagen or said carboxyl propeptide region has been substituted with a peptide which does not inhibit fibril-formation and which is capable of forming a trimer.

19. A method for producing a trimeric chimera protein wherein a trimeric chimera protein of claim 2 is produced by ligating a gene coding for a procollagen and a gene coding for a biologically active peptide by genetic engineering means, and expressing the ligation product using a recombinant protein expression system.

20. A method for producing a trimeric chimera protein wherein a trimeric chimera protein of claim 3 is produced by ligating a gene coding for a procollagen and a gene coding for a biologically active peptide by genetic engineering means, and expressing the ligation product using a recombinant protein expression system.

21. A method for producing a trimeric chimera protein wherein a trimeric chimera protein of claim 4 is produced by ligating a gene coding for a procollagen and a gene coding for a biologically active peptide by genetic engineering means, and expressing the ligation product using a recombinant protein expression system.

22. A vector for expressing a trimeric chimera protein of claim 2, said vector containing a gene coding for a procollagen and a gene coding for a biologically active peptide.

23. A vector for expressing a trimeric chimera protein of claim 3, said vector containing a gene coding for a procollagen and a gene coding for a biologically active peptide.

24. A vector for expressing a trimeric chimera protein of claim 4, said vector containing a gene coding for a procollagen and a gene coding for a biologically active peptide.

25. A cell for producing a trimeric chimera protein of claim 2, said cell having a vector containing a gene coding for a procollagen and a gene coding for a biologically active peptide.

26. A cell for producing a trimeric chimera protein of claim 3, said cell having a vector containing a gene coding for a procollagen and a gene coding for a biologically active peptide.

27. A cell for producing a trimeric chimera protein of claim 4, said cell having a vector containing a gene coding for a procollagen and a gene coding for a biologically active peptide.

* * * * *